United States Patent
Konrad

(10) Patent No.: US 9,757,833 B2
(45) Date of Patent: Sep. 12, 2017

(54) ADAPTER FOR A DENTAL MILLING BLOCK HOLDER AND A WORKPIECE HOLDER

(71) Applicant: Ivoclar Vivadent AG, Schaan (LI)

(72) Inventor: Erich Konrad, Feldkirch (AT)

(73) Assignee: Ivoclar Vivadent AG, Schaan (LI)

(*) Notice: Subject to any disclaimer, the term of this patent is extended or adjusted under 35 U.S.C. 154(b) by 0 days.

(21) Appl. No.: 14/838,821

(22) Filed: Aug. 28, 2015

(65) Prior Publication Data

US 2016/0158903 A1 Jun. 9, 2016

Related U.S. Application Data

(63) Continuation-in-part of application No. 29/519,833, filed on Mar. 9, 2015.

(30) Foreign Application Priority Data

May 22, 2015 (EP) .................................. 15168860

(51) Int. Cl.
*B23Q 3/10* (2006.01)
*A61C 13/00* (2006.01)
*A61C 13/12* (2006.01)

(52) U.S. Cl.
CPC .......... *B23Q 3/103* (2013.01); *A61C 13/0022* (2013.01); *A61C 13/12* (2013.01)

(58) Field of Classification Search
CPC ........... B23Q 3/108; B25B 5/125; B25B 5/10; A61C 13/0022; A61C 13/12

USPC ............................................. 269/309, 74, 76
See application file for complete search history.

(56) References Cited

U.S. PATENT DOCUMENTS

| | | | | |
|---|---|---|---|---|
| 1,427,153 A * | 8/1922 | Fisher | ................. | B25H 1/0007 269/296 |
| 1,705,629 A * | 3/1929 | Wildbore | ............... | B23Q 3/103 269/151 |
| 2,047,222 A * | 7/1936 | Poorman | ............... | B23B 29/248 82/157 |
| 3,245,678 A * | 4/1966 | Riehle | .................... | B23Q 3/103 269/257 |

(Continued)

FOREIGN PATENT DOCUMENTS

| | | | | |
|---|---|---|---|---|
| DE | WO 0034625 A1 * | 6/2000 | ............. | B28D 1/188 |
| DE | 102008030050 A1 | 8/2009 | | |

(Continued)

*Primary Examiner* — George Nguyen
(74) *Attorney, Agent, or Firm* — Ann M. Knab; Thad McMurray

(57) ABSTRACT

The invention provides an adapter for a dental milling block holder with a dental milling block (52 and 54) or dental grinding block, which is attached to a dental milling block holder, in particular glued on, wherein the dental milling block holder is provided with a round shank which is mounted in the adapter (40). It is characterized in that the adapter (40) is provided with at least one internal thread (92) for the mounting of a fastening screw (31) which acts on the shank, to which fastening screw (31) inside the shank mount of the adapter (40) of the fastening screw (31) positioned opposite of it, at least one in particular elevated, in particular at least two elevated clamping surfaces (74 and 76) are formed against which the shank abuts.

24 Claims, 7 Drawing Sheets

(56) References Cited

U.S. PATENT DOCUMENTS

Figure 1:
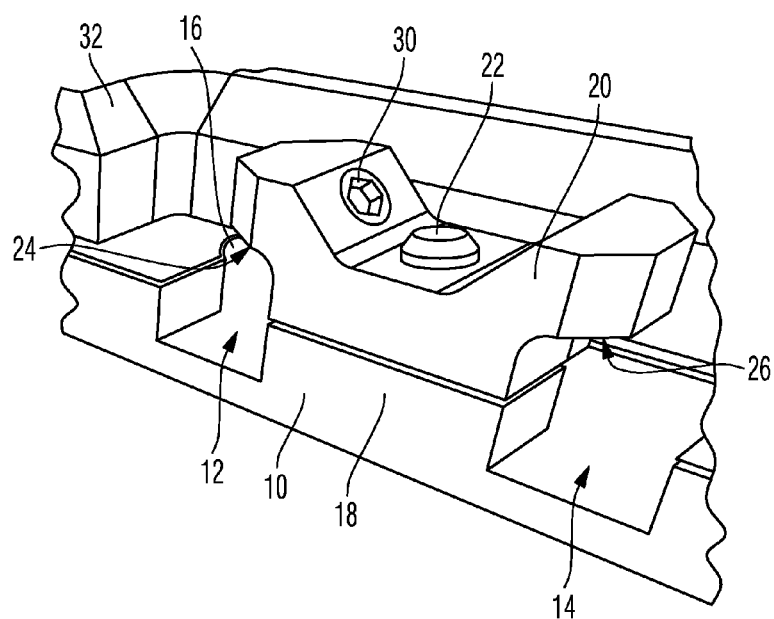

| | | | |
|---|---|---|---|
| 5,918,867 A * | 7/1999 | Goodyear | B23Q 1/5412 |
| | | | 269/71 |
| 6,254,077 B1 * | 7/2001 | Riley, Jr. | B25B 5/10 |
| | | | 269/156 |
| 8,152,151 B2 * | 4/2012 | Sandmeier | B23B 31/1078 |
| | | | 269/20 |
| 8,492,624 B1 | 7/2013 | Carrigan | |
| 8,820,726 B2 | 9/2014 | Yeom | |
| 2005/0276672 A1 * | 12/2005 | Prince | A61C 13/0022 |
| | | | 409/234 |
| 2007/0063456 A1 * | 3/2007 | Troxler | B23H 7/26 |
| | | | 279/156 |
| 2009/0130634 A1 | 5/2009 | Ganley et al. | |
| 2010/0219573 A1 * | 9/2010 | O'Rell | B23Q 1/42 |
| | | | 269/246 |
| 2012/0214133 A1 | 8/2012 | Jung | |

FOREIGN PATENT DOCUMENTS

| | | |
|---|---|---|
| DE | 102007043837 B4 | 2/2014 |
| EP | 0480209 A1 | 4/1992 |
| KR | 101333416 B1 | 11/2013 |
| TW | 201444537 A | 12/2014 |
| WO | 0209612 A1 | 2/2002 |

* cited by examiner

ADAPTER FOR A DENTAL MILLING BLOCK HOLDER AND A WORKPIECE HOLDER

This present application claims priority to European patent application No. 15168860.3, filed on May 22, 2015, and this present application also claims priority to U.S. design patent application Ser. No. 29/519,833 filed on Mar. 9, 2015, which claims priority to WO 857208301 filed on Dec. 4, 2014, the disclosures all of which are incorporated herein by reference in their entirety.

The invention concerns an adapter for a dental milling block holder as well as a workpiece holder, in accordance with the attached claims, wherein here the term "milling block" just like the process of milling in general is supposed to also include any types of machining processes, in particular also grinding, with a particular emphasis on the milling of dental restorations from blanks and with a particular emphasis on the milling of ceramics and ceramic blocks.

Dental restorations made out of ceramics—but frequently also made out of plastics or composites—are often produced in machine tools with several axes in which a blank is machined or cut. Such a machine tool can, for example, be a milling machine with four axes or five axes. The dental ceramics to be milled can be present as a blank in the form of a round disc, or as a block-shaped blank, which is adhesively bonded to a block holder. Such a block is typically of rectangular shape with rounded corners.

For guiding and holding in the dental milling machine, a workpiece holder with two clamping bars positioned opposite of each other is often provided, which then holds four, six or also eight blanks clamped, wherein the shanks of the dental milling block holders are mounted at clamping holders, which is done in such a fashion that half of the blanks are positioned opposite of the other half of the blanks, and the free ends of the blanks each point in the direction towards one another.

The holder must withstand considerable forces, corresponding to the forces acting during processing by the dental milling machine or the dental grinding machine. If it is of circular shape, it is necessary to make sure, with the help of an anti-turn locking device, that the blank or the milling block does not rotate together with its holder during operation. This risk does not exist if a rectangular cross-section is selected for the holder which acts together with a corresponding workpiece mount. As a result, such a holder mount has proven particularly successful and is used frequently too.

In order to prevent any bearing clearance, at least one slanted surface is preferably provided with such a holder, on which slanted surface the clamping pressure of the clamping holder is exerted, such that the bearing forces are mainly absorbed between the slanted surface and the opposite corner, or the side surfaces of the holder adjacent to it, respectively.

Even if such a holder is particularly good from a technical point of view, round holders with smaller cross-sections are frequently used for cost reasons. With these, the rotation prevention is typically put into practice with the help of a short groove inside the flange of the holder with which a corresponding nose of the workpiece holder is supposed to engage.

If, however, the user does not insert the holder far enough, there is the risk of the nose not locking in with the groove. In this case, there is no rotation prevention, and if the clamping force is not sufficient, there is a considerable risk of the holder slightly rotating during the process of milling of the blank.

This holds true in particular if the anti-turn locking device—which is per se favourable for reasons of improved torque transmission—is attached to the flange of the holder which typically has a limited thickness of, for instance, 1 mm.

Whereas a high degree of rotation is immediately noticeable from the poor result of the milling process, there is the risk in case of only slight rotation by, for example, 1° to 2° that the dental restoration, such as, for instance, a crown which is to be manufactured, is malformed, which may have adverse effects either on occlusion, on retention, or also on aesthetics, or on various ones of these aspects.

A particular type of anti-turn locking device can for example be taken from EP 0 480 209 A1. With this solution, a distinct neck is provided in the holder, which, however, makes the holder as a whole subject to breaking at this position.

Another example for a solution with a formative rotation prevention is the solution known from WO 2002/09612 A1. There the holder is shaped hexagonally, which provides six different insertion positions in the workpiece mount for the user.

Blanks are frequently—as can also be taken from FIGS. 4a and 4b of WO 2002/09612 A1—of rectangular shape and have different transverse dimensions, i.e. a length different from their width.

In particular with the above workpiece mounts with four, six or even eight insertion positions, it is favourable, on the other hand, if insertion positions can be taken which are displaced by 90° relative to one another. This is something the holder known from WO 2002/09612 A1 is not able to achieve, for it allows only insertion positions at angles of 60° or 120°, respectively, but not at an angle of 90°.

Adapters for holders have also been known for a longer time already, for circular holders, for example, the adapter known from DE 10 2007 043 837 B4 and corresponding U.S. Pat. No. 8,492,624, which is hereby incorporated by reference. In this solution, the holder is inserted into the adapter in a clamping fashion, wherein the rather low degree of thickness of the material of the blind hole of the adapter there is made use of in order to provide clamping elasticity.

Such a solution is basically particularly favourable for providing the tight-fit between different workpiece mounts and holders. It can also be employed in case of tight spatial conditions, for the holder is entirely mounted inside the adapter. The durability in case of frequent change of adapter, however, could be better, and rotation prevention depends strongly on how far the holder and the blind hole of the adapter deviate from the circular shape.

In contrast to this, the invention is based on the task of creating an adapter for a dental milling block holder and a related workpiece holder in accordance with the claims which is even improved with respect to durability, and is even better adaptable as well.

This task is solved, in accordance with the invention, by the independent claims. Advantageous further embodiments result from the subordinate claims.

In accordance with the invention, it is intended with an adapter for a dental milling block holder in one embodiment to use a free portion of the circumference of the workpiece mount in order to put into practice there a thickening of material and mount a fastening screw there.

This is guided in an internal thread of the adapter, which has 5, in particular 8 to 10, thread pitches, in order to be able to apply the necessary fastening strength, and fixes the holder directly.

The fastening screw acts on the holder which is provided with a round shank. The clamping force is exerted between the fastening screw and preferably at least two elevated clamping surfaces which are situated diametrically opposite of the fastening screw.

In accordance with the invention, the 90° displacement between the clamping adapter/holder and adapter/workpiece mount results in a particularly favourable force distribution. The rather punctual introduction of force creates a comparatively high pressure and insofar also supports rotation prevention. The solution in accordance with the invention is insofar more stable and more independent of whether a retaining nose has entered into a corresponding groove at the holder.

In particular the clamping screw can, in accordance with the invention, be produced out of a comparatively hard material which can also easily enter into the material of the holder with its tip. As a result, insofar beside the force fit, an additional positive connection is created, which also supports rotation prevention. It is particularly favourable if also the adapter consists of a hardened material and thus a precise bearing fit is guaranteed also in the long term.

It is particularly favourable if the fastening screw and/or the clamping screw and/or the retaining screw are shaped as a grub or headless screw.

In a favourable embodiment of the invention, it is intended to design the adapter in two shapes, namely with a retaining nose which extends at an angle of 45° clockwise in relation to the fastening screw, and with a retaining nose which extends at an angle of 45° anti-clockwise in relation to the fastening screw. The two retaining noses are then displaced, observed against each other, by 90°, and one of the adapters makes possible a bearing position of the rectangular-shaped dental milling block which is displaced by 90° relative to the other adapter, which dental milling block can be formed—as far as its shape is concerned—in accordance with WO 2002/09162 A1.

In another favourable embodiment, it is intended to form the fastening screw and the clamping screw as one single screw which then penetrates the adapter. At this position, the adapter is then free of any internal thread, and the clamping-fastening screw is guided in the clamping hold-down. In this fashion, the force introduced onto the holder then presses the latter against the two elevated clamping surfaces at the opposite side, and via these at the same time the adapter into the opposite corner.

Depending on the design of the holder, it is favourable to explicitly provide one or two clamping surfaces which offer the desired counter-force in the abutment and the associated static friction. It is essential too in this connection that the starting point of the fastening screw and the clamping surface or the clamping surfaces are positioned diametrically opposite of each other. Preferably, two clamping surfaces are provided which extend, with relation to the internal thread and its axis, respectively, at an angle of 135° to the latter, one clockwise and the other one anti-clockwise.

The clamping surfaces then extend each around this 135° position, for instance over an angular range of 24°, i.e. from 123° to 147°, with reference to the point of impact of the axis of the fastening screw on the shank mount of the adapter.

If the shank mount is of circular shape, the clamping surfaces can simply be formed as straight surfaces which are elevated with relation to the circular shape, such that the shank mount has a segmental shape at each of these positions.

Clamping surfaces such formed are particularly well suited for absorbing the clamping forces needed with good static friction, wherein it is to be understood that also any other clamping surfaces can be put into practice, provided these are positioned opposite of the fastening screw inside the shank mount.

It is particularly favourable to provide the fastening screw with a pointed cone which can enter into the material of the shank of the holder. With this solution, the dental milling block can simply be removed from the holder mount, i.e. the workpiece mount, together with the holder and the adapter.

Another advantage of the adapter in accordance with the invention is its symmetrical construction. The shank of the holder can thus be inserted into both sides of the adapter—and also be fixed with the help of the fastening screw. As a result of the anti-turn locking device in accordance with the invention, the dental milling block can then be fixed in the 90° position or in the 0° position as desired at both of the opposite clamping bars, wherein it is to be understood that also the orientational nose is provided doubly, i.e. symmetrically, as an anti-turn locking device.

The projection in accordance with the invention in which the fastening screw is guided in one embodiment also offers the possibility of forming a gripping manubrium once the adapter has been fixed in the clamping holder without the dental milling block, for example when the dental milling block together with its holder is to be mounted later, which is, without adapter.

It is insofar particularly favourable that the projection of the adapter is provided at a position that is free of any clamping forces as far as the clamping holder bearing is concerned.

Preferably, the clamping force is applied in a direction which is displaced by 90° compared with that, and between portions of the adapter which are positioned opposite of each other, which adapter is held between the clamping hold-down and the opposite corner with the help of a clamping screw. For this purpose, the adapter is provided—at the side which is adjacent to the clamping hold-down—with a slanted surface which corresponds with a corresponding slanted surface of the clamping hold-down.

Figure 2:
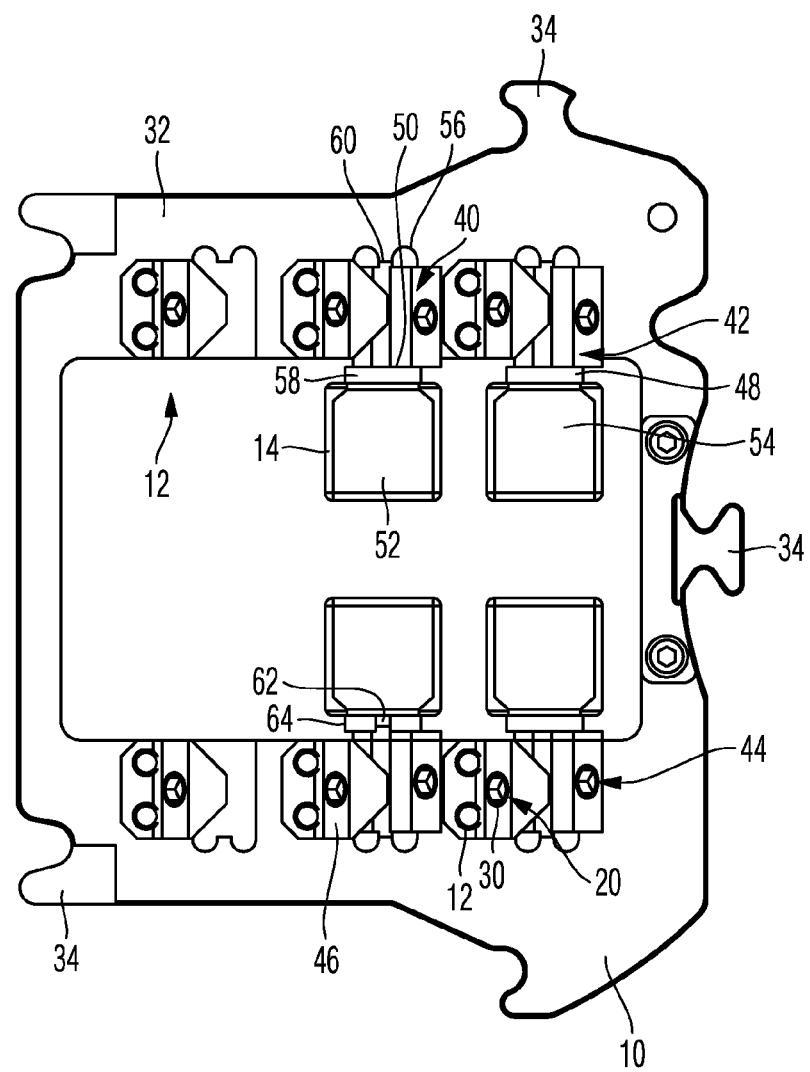
Figure 3:
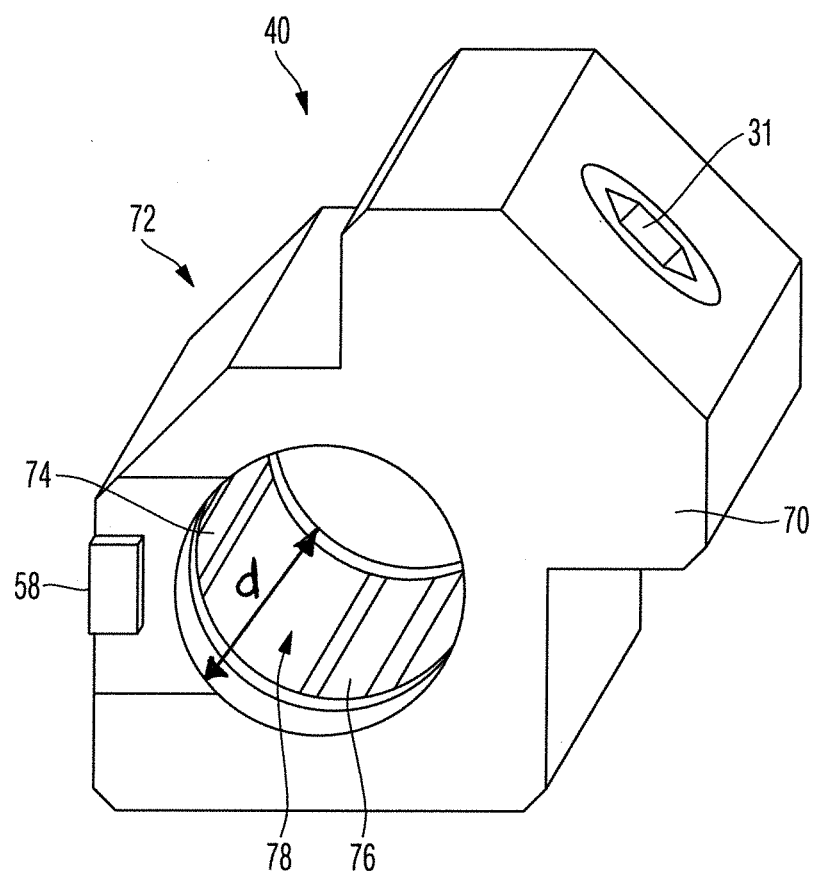
Figure 4:
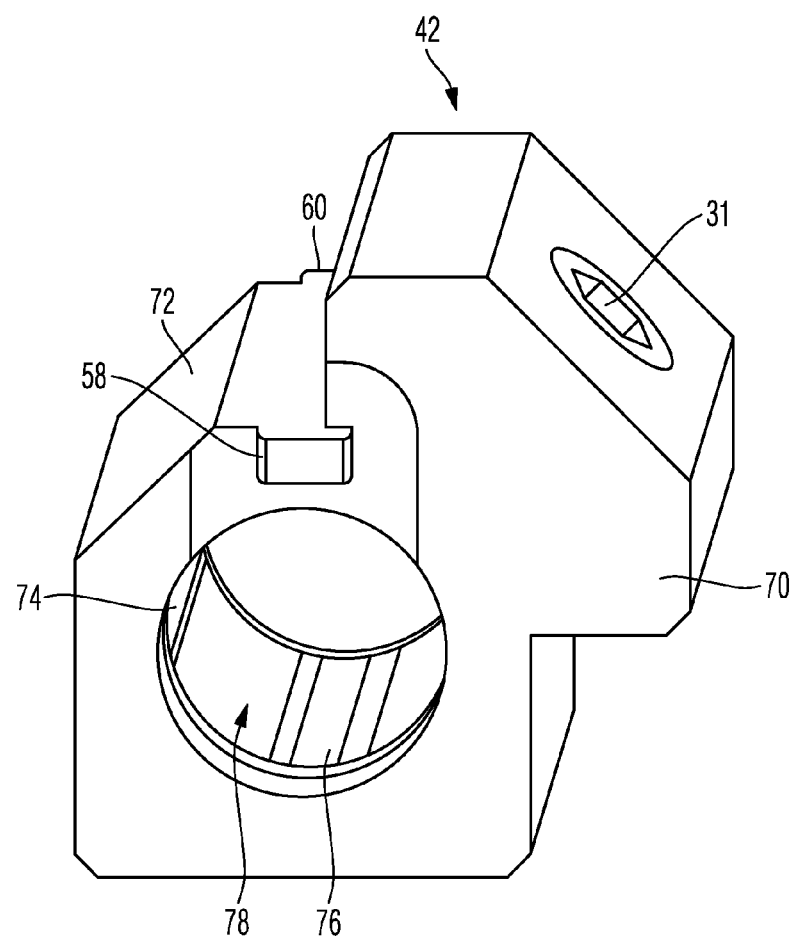
Figure 5:
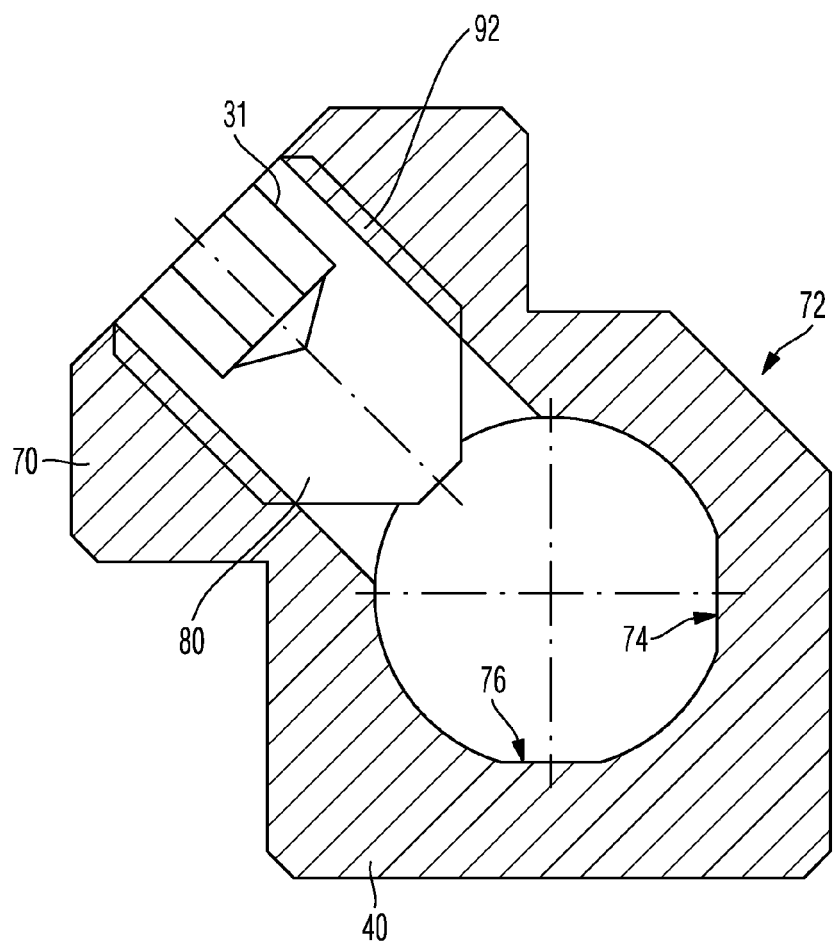
Figure 6:
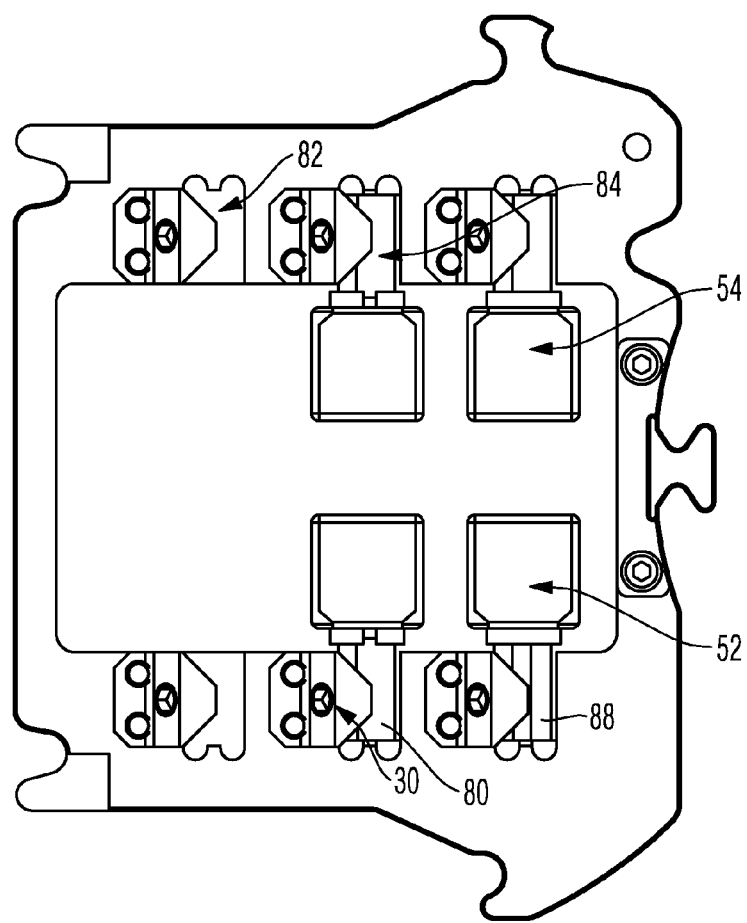
Figure 7:
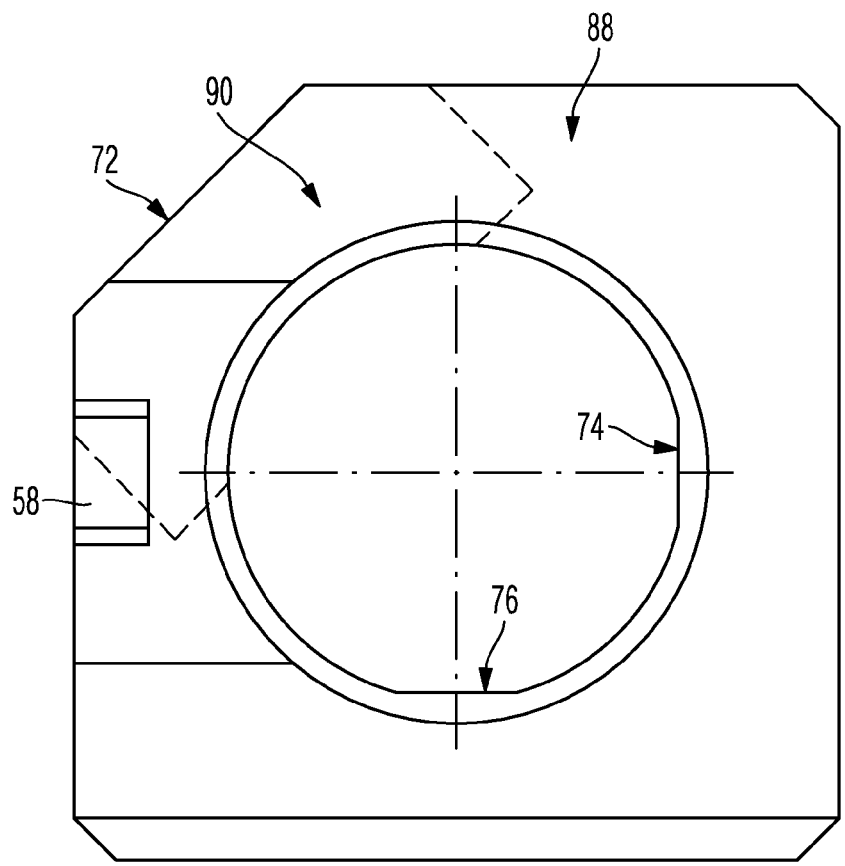

Further advantages, details and features of the invention result from the subsequent description of several embodiments of the invention with the help of the drawings, which show:

FIG. 1 a schematic detailed view of a workpiece holder in accordance with the invention, however without the adapter for a dental milling block holder and the dental milling block holder as well as without the dental milling block either;

FIG. 2 a top view of a workpiece holder in accordance with the invention;

FIG. 3 a perspective view of an adapter for a dental milling block holder in accordance with the invention in one embodiment;

FIG. 4 the adapter for a dental milling block holder in accordance with FIG. 3, however in a different embodiment;

FIG. 5 a cut through an embodiment of an adapter for a dental milling block holder in accordance with the invention;

FIG. 6 a top view onto a workpiece holder in accordance with the invention, however in a different embodiment; and FIG. 7 a front view of a different embodiment of an adapter for a dental milling block holder in accordance with the invention.

In FIG. 1, portions of a workpiece holder 10 are depicted in perspective. Workpiece holder 10 is provided, in the portion depicted, with two holder mounts 12 and 14 which are formed as rectangular-shaped recesses in a base plate of the workpiece holder. The holder mounts are of essentially rectangular shape, with the exception of an additional recess 16, which can, for instance, serve for the purpose of receiving chippings or grinding dust during the machining process.

Between holder mounts 12 and 14, the base plate forms sort of a central pole 18. This supports a clamping hold-down 20 which is supported by a central retaining screw 22 on workpiece holder 12 or its base plate, respectively.

Clamping hold-down 20 is provided with a slanted surface 24 above holder mount 12, which faces holder mount 12, and a slanted surface 26 above holder mount 14, which faces holder mount 14. Slanted surfaces 24 and 26 cover each of the related holder mounts 12 and 14 about halfway. They extend at an angle of 45° relative to the vertical, for instance relative to the layer spanned by workpiece holder 10. In order to prevent notching effects, the transition between the vertical arm of clamping hold-down 20 and the slanted surface concerned is rounded out by a cove.

Holder mounts 12 and 14 are intended to mount dental milling block holders, to be more precise, their shanks, safely guided. Accordingly, the shanks are formed essentially with the same geometrical dimensions as holder mounts 12 and 14, which is, with corners. One slanted surface corresponding to slanted surfaces 24 and 26, respectively, is provided each at one shank. The lateral guidance in both directions is predetermined by holder mounts 12 and 14, all the more because a rather low degree of bearing clearance is intended at this position, for instance 50 μm. Slanted surfaces 24 and 26, however, perform a holding function by pressing the shanks into the corners which are respectively facing away from slanted surfaces 24 and 26. For this purpose, each slanted surface is provided with a clamping screw 30 passing through clamping hold-down 20, wherein only clamping screw 30 of slanted surface 24 is visible from FIG. 1; in practice a corresponding clamping screw is provided as a grub or headless screw also in slanted surface 26 and passing through clamping hold-down 20 as well.

Workpiece holder 10 is further provided with a clamping frame 32. This carries not depicted clamping elements at which workpiece holder 10 is guided at a workpiece guide with two or three axes of the associated dental milling machine.

From FIG. 2 a corresponding workpiece holder 10 is visible in a top view. Equal reference numbers indicate equal parts here as well as in the further Figures. As can be seen, a number of clamping elements 34 are spread at clamping frame 32 of workpiece holder 10. Also several, i.e. a total of six, holder mounts 12 are spread at the annular clamping frame. These point each towards the inside, wherein three holder mounts are positioned opposite of the other three holder mounts, and two holder mounts each are aligned coaxially with relation to each other.

The holder mounts are intended for the mounting of shanks of dental milling blocks. In accordance with the invention, adapters for dental milling block holders 40, 42, 44 and 46 are provided which have the design better visible from FIGS. 3 and 4. This adapter for a dental milling block holder 40 to 46 is formed in such a fashion that it fits into the associated holder mount, for example holder mounts 12 and 14, respectively, and mounts in it a round shank of the associated dental milling block holder. The circular shank runs out each in a flange 48 and 50, respectively, which is somewhat thicker compared with the diameter of the shank, and which supports the associated dental milling block 52 and 54, respectively.

It can be taken from FIG. 2 that in this depiction, dental milling block 52 is narrower compared with dental milling block 54. Indeed, dental milling block 54 is rotated by 90° in relation to dental milling block 52, however it has the same dimensions per se. As an anti-turn locking device, the associated flange 48 and 50, respectively, is provided with a groove, wherein groove 56 is visible from FIG. 2. There an orientational nose 58 of adapter 40 is entering. A corresponding nose can also be found at adapter 42, but displaced by 90°, as results from the comparison of FIGS. 3 and 4.

Positioned opposite of orientational nose 58, another orientational nose 60 is provided. This is employed in the assemblaged position of adapter 46 and there engages with an associated groove 62 of flange 64.

This means that adapter 40 exactly corresponds to adapter 46, while adapter 42 corresponds to adapter 44.

As can furthermore be taken from FIG. 2, the local clamping hold-downs 20 are not formed symmetrically corresponding to FIG. 1, such that one clamping hold-down fixes two dental milling block adapters each. Rather, one clamping hold-down 20 is provided per holder mount, which clamping hold-down is attached with the help of two retaining screws 22 with workpiece holder 10 otherwise.

From FIG. 3, the embodiment of an adapter for a dental milling block holder 40 can be taken. Fastening screw 31 is guided in a projection 70, which is of an essentially triangular cross section, and penetrates it. Displaced at an angle of 90° relative to projection 70, slanted surface 72 is provided which is intended for the abutment against slanted surface 26.

When the circular shank of the dental milling block holder has been inserted into adapter 40, clamping screw 30 is fastened. It then presses the shank against two clamping surfaces 74 and 76 which extend at a symmetrical angle relative to fastening screw 31. Clamping surfaces 74 and 76 are formed as planar surfaces which protrude compared with the otherwise circular shank mount 78 of adapter 40; whose radius is 0.1 cm larger than the radius of the shank. A reception depth d of the adapter 40 is slightly less the length of the round shank of the of the holder. Preferably, the reception depth d of the adapter 40 is 10% to 40% less than the length o the round shank of the holder.

Orientational nose 58 extends in the embodiment of adapter 40 depicted at the position at which also clamping surface 74 is provided inside.

This is a difference from the other embodiment of adapter 42 which can be taken from FIG. 4. There, orientational nose 58 extends displaced by 90° compared with the embodiment in accordance with FIG. 3, i.e. is positioned diametrically opposite of clamping surface 76.

A corresponding orientational nose 60 is provided at the back surface of adapter 42, while the opposite orientational nose to orientational nose 58 is not visible from FIG. 3 in the Figure.

It can be taken from FIG. 5 in what fashion clamping screw 30 of adapter 40 penetrates projection 70. It is provided with a pointed cone 80 which is intended for intensively pressing the shank of the dental milling block holder against slanted surfaces 74 and 76 with its tip.

From FIG. 6, another embodiment of an adapter for a dental milling block holder in accordance with the invention and of the associated workpiece holder, are visible respectively. The associated adapter 82, 84, 86 and 88, respectively, is not provided with any separate clamping screws 30 or fastening screws 31, respectively; rather the local clamping screw 30 passes through adapter 88 and acts directly on the shank.

From FIG. 7, a correspondingly modified embodiment of an adapter 88 can be taken. A passage recess 90 is provided which penetrates slanted surface 72 and is intended for the mounting of the associated clamping screw 30.

While clamping screw 31 in accordance with FIG. 5 is guided in the internal thread 92 there of adapter 40, adapter 88 in this embodiment is not provided with a thread, and the guidance of the associated clamping screw is done in the associated clamping hold-down 20.

Also with the embodiment in accordance with FIGS. 6 and 7, orientational noses are provided, wherein orientational nose 58 is visible form FIG. 7. Furthermore, also clamping surfaces 74 and 76 are provided which are intended for the abutment against the shank of the associated dental milling block holder and make possible a safe clamping of the dental milling block holder at the workpiece holder in one go.

The invention claimed is:

1. Adapter for a dental milling block holder with a dental milling block or dental grinding block attached to a dental milling block holder, wherein the dental milling block holder is provided with a round shank which is mountable in the adapter wherein the adapter comprises:
   a shank mount for mounting the round shank, and
   an internal thread for mounting a fastening screw which acts on the shank,
   wherein the shank mount comprises at least two elevated clamping surfaces which are positioned opposite the fastening screw for abutment against the shank.

2. Adapter for a dental milling block holder in accordance with claim 1, wherein the dental milling block or dental grinding block is attached to the dental milling block holder by glue.

3. Adapter for a dental milling block holder in accordance with claim 1, wherein the adapter is provided with at least one protruding orientational nose which is intended to enter into a groove of the milling block holder.

4. Adapter for a dental milling block holder in accordance with claim 1, wherein the fastening screw is provided with a pointed cone and comprises a material which is harder than the material of the milling block holder.

5. Adapter for a dental milling block holder in accordance with claim 1, wherein the shank mount of the adapter is provided with a radius which is larger than half a diameter of the round shank, and the round shank can be introduced into the shank mount at the elevated clamping surfaces with a very small clearance of less than 50 μm.

6. Adapter for a dental milling block holder in accordance with claim 1, wherein the shank mount of the adapter is provided with a radius which is approximately 0.1 mm larger, than half the diameter of the round shank.

7. Adapter for a dental milling block holder in accordance with claim 1, wherein the adapter is provided with a shank mount which is formed as a passage recess, and that the round shank of the holder can be inserted at both sides of this passage recess.

8. Adapter for a dental milling block holder in accordance with claim 1, wherein a reception depth of the adapter is slightly less than the length of the round shank of the holder, and the fastening screw is mounted inside the adapter with the help of the internal thread in a centrally symmetrical fashion and acts on the round shank slightly distally from its centre.

9. Adapter for a dental milling block holder in accordance with claim 1, wherein a reception depth of the adapter is 10% to 40% less than the length of the round shank of the holder.

10. Workpiece holder comprising an adapter for a dental milling block holder with a dental milling block or dental grinding block, which is attached to a dental milling block holder, wherein the dental milling block holder is provided with a round shank which is mounted in the adapter wherein the adapter comprises a shank mount for mounting the round shank, and an internal thread for mounting a fastening screw which acts on the shank, wherein the shank mount comprises at least two elevated clamping surfaces which are positioned opposite the fastening screw for abutment against the shank.

11. Workpiece holder in accordance with claim 10, wherein the workpiece holder comprises a clamping hold-down with a first slanted surface that acts on the clamping hold-down, and wherein the adapter is mounted in the clamping hold-down located in the workpiece holder.

12. Workpiece holder in accordance with claim 11, wherein the first slanted surface of the clamping hold-down is facing towards a second slanted surface of the adapter, and a clamping screw passes through the first slanted surface.

13. Workpiece holder in accordance with claim 10, wherein two adjacent mounts of the workpiece holder are partly covered by a clamping hold-down which extends symmetrically with two slanted surfaces pointing diagonally away from each other and is retained by a common retaining screw on the workpiece holder.

14. Workpiece holder in accordance with claim 10, wherein the workpiece holder is provided with at least two adjacent holder mounts which extend essentially in parallel with each other and are partly covered by a common clamping hold-down.

15. Workpiece holder in accordance with claim 11, wherein the fastening screw is positioned in such a fashion that it is displaced by 90° with relation to a second slanted surface of the adapter and passes through a projection which is attached to the adapter.

16. Workpiece holder in accordance with claim 10, wherein a clamping screw of a clamping hold-down acts on the shank through the adapter and forms the fastening screw.

17. Workpiece holder in accordance with claim 10, wherein the adapter is provided with at least one protruding orientational nose which is adapted to enter into a groove of the milling block holder.

18. Workpiece holder in accordance with claim 17, wherein two adapters are provided with orientational noses that are displaced by 90° with relation to one another.

19. Workpiece holder in accordance with claim 10, wherein the fastening screw is provided with a pointed cone and comprises a material which is harder than the material of the holder.

20. Workpiece holder in accordance with claim 10, wherein the shank mount of the adapter is provided with a radius which is larger than half a diameter of the round shank, and the round shank can be introduced into the shank mount at the elevated clamping surfaces with a very small clearance of less than 50 μm.

21. Workpiece holder in accordance with claim 10, wherein the dental milling blocks are formed as rectangular blocks with a longer and a shorter side, and the assemblage in the workpiece holder mount can be in an upright fashion or in a horizontal fashion, relative to the longer side, according to the choice of the user.

22. Workpiece holder in accordance with claim 10, wherein the adapter is provided with a shank mount that is formed as a passage recess, and that the shank of the holder can be inserted at either side of the passage recess.

23. Workpiece holder in accordance with claim 10, wherein the reception depth of the adapter is slightly less than the length of the shank of the holder, and the fastening screw is mounted inside the adapter with the help of the internal thread in a centrally symmetrical fashion and acts on the shank slightly distally from the center of the fastening screw.

24. Workpiece holder in accordance with claim 23, wherein the reception depth of the adapter is 10% to 40% less than the length of the shank of the holder.

\* \* \* \* \*